(12) United States Patent
Hafey et al.

(10) Patent No.: US 7,890,498 B1
(45) Date of Patent: Feb. 15, 2011

(54) USER INTERFACE FOR A MEDICAL INFORMATICS SYSTEM THAT INCORPORATES AN EXAMINATION TIMELINE

(75) Inventors: Christopher Hafey, San Francisco, CA (US); Jonathon Reis, Saratoga, CA (US); Ton van den Hoven, San Mateo, CA (US); Tongzhe Cui, San Jose, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 882 days.

(21) Appl. No.: 10/305,423

(22) Filed: Nov. 25, 2002

Related U.S. Application Data

(60) Provisional application No. 60/333,570, filed on Nov. 26, 2001.

(51) Int. Cl.
G06F 7/00 (2006.01)
(52) U.S. Cl. .................................................... 707/722
(58) Field of Classification Search .......... 707/1–104.1, 707/722
See application file for complete search history.

(56) References Cited

U.S. PATENT DOCUMENTS

| | | | | |
|---|---|---|---|---|
| 5,431,161 A | | 7/1995 | Ryals et al. ................. | 600/425 |
| 5,452,416 A | * | 9/1995 | Hilton et al. ................ | 715/783 |
| 5,542,003 A | | 7/1996 | Wofford ...................... | 382/132 |
| 5,680,152 A | | 10/1997 | Bricklin ....................... | 345/419 |
| 5,724,985 A | * | 3/1998 | Snell et al. .................. | 600/510 |
| 5,779,634 A | * | 7/1998 | Ema et al. ................... | 600/407 |
| 5,954,650 A | | 9/1999 | Saito et al. .................. | 600/425 |
| 5,986,662 A | | 11/1999 | Argiro et al. ................ | 345/424 |
| 5,987,345 A | | 11/1999 | Engelmant et al. .......... | 600/407 |
| 6,032,120 A | * | 2/2000 | Rock et al. ...................... | 705/2 |

(Continued)

FOREIGN PATENT DOCUMENTS

JP 10225441 8/1998

(Continued)

OTHER PUBLICATIONS

Stentor, "iSite Medical Image and Information Management System", Oct. 2001, retrieved from http://web.archive.org/web/20011031120001/http://stentor.com/index.html on Sep. 30, 2009. 28 pages.*

(Continued)

*Primary Examiner*—Hung T Vy
*Assistant Examiner*—Michael Le

(57) ABSTRACT

A user interface for a medical informatics system displays medical information including information regarding medical examinations. A patient history timeline and a relevant exams timeline, which include a plurality of elements, are displayed such that an element represents a medical examination. A position of an element on the timeline indicates an acquisition time for a medical examination relative to other medical examinations on the timeline. An element displays information about a corresponding medical examination, including: a date, to indicate acquisition of the medical examination; information to indicate whether images are available for the corresponding medical examination; and information to indicate whether a report is available for the corresponding medical examination. A user may extract additional information about an exam through use, of a cursor control device, including: information to indicate a location of images for a medical examination; general information about the medical examination; and a plurality of menu items to permit a user to select functions for the medical examination.

48 Claims, 3 Drawing Sheets

U.S. PATENT DOCUMENTS

| | | | |
|---|---|---|---|
| 6,061,062 A * | 5/2000 | Venolia | 715/856 |
| 6,144,971 A * | 11/2000 | Sunderman et al. | 715/500 |
| 6,177,937 B1 | 1/2001 | Stockham et al. | 715/807 |
| 6,269,379 B1 | 7/2001 | Hiyama et al. | 700/104.1 |
| 6,363,393 B1 * | 3/2002 | Ribitzky | 707/102 |
| 2001/0041992 A1 * | 11/2001 | Lewis et al. | 705/3 |
| 2002/0021828 A1 * | 2/2002 | Papier et al. | 382/128 |
| 2002/0029157 A1 * | 3/2002 | Marchosky | 705/3 |
| 2002/0046062 A1 * | 4/2002 | Kameda | 705/3 |
| 2002/0065854 A1 * | 5/2002 | Pressly | 707/530 |
| 2002/0077863 A1 * | 6/2002 | Rutledge et al. | 705/3 |
| 2002/0082865 A1 * | 6/2002 | Bianco et al. | 705/2 |

FOREIGN PATENT DOCUMENTS

| | | |
|---|---|---|
| JP | 11290279 | 10/1999 |

OTHER PUBLICATIONS

Healthcare IT, "Torrance Memorial Medical Center, The Benefits of Enterprise-wide PACS", Nov. 2005, 4 pages.*

Brian Casey, "Stentor Releases iSite Enterprise 2.0", May 6, 2001, 1 page.*

* cited by examiner

USER INTERFACE FOR A MEDICAL INFORMATICS SYSTEM THAT INCORPORATES AN EXAMINATION TIMELINE

CROSS-REFERENCES TO RELATED APPLICATIONS

This application claims the benefit of U.S. Provisional Patent Application No. 60/333,570, filed Nov. 26, 2001, entitled "User Interface For A Medical Informatics System That Incorporates An Examination Timeline."

BACKGROUND OF THE INVENTION

1. Field of the Invention

The present invention is directed toward the field of medical informatics, and more particularly toward displaying information regarding medical examinations on a timeline.

2. Art Background

Radiology equipment (e.g., CT scanners, MRI scanners, X-Ray etc.) is in wide spread use as diagnostic tools in hospitals today. Traditionally, radiology departments utilize equipment, such as X-Ray machines, that generate images on film. Typically, when collecting information from a diagnostic tool, several medical images are generated for subsequent analysis and diagnosis of the patient's medical condition. This collection of medical images may be referred to as an examination or "exam." For example, an exam from an X-Ray machine may consist of a number of X-Rays taken from different perspectives of the target area. It is the totality of the exam that the physician uses to make a diagnosis of the patient.

It has become more common in the medical field for images to be stored, distributed, and viewed in digital form using computer technology. Currently, Picture Archival and Communication Systems or PACS have been in widespread use. In a typical PACS application, image data obtained by imaging equipment such as CT scanners or MRI scanners are stored in the form of computer data files. The size of a data file for an image varies depending on the size and resolution of the image. For example, a typical image file for a diagnostic-quality chest X-ray is on the order of 10 megabytes (MB). The image data files are usually formatted in a "standard" or widely accepted format. In the medical field, one widely used image format is known as DICOM. The DICOM image data files are distributed over computer networks to specialized viewing stations capable of converting the image data to high-resolution images on a CRT display.

The present invention enhances the ability to work with a medical informatics system by providing an efficient means to view exams for a patient.

SUMMARY OF THE INVENTION

A user interface for a medical informatics system displays medical information including information regarding medical examinations. A timeline, which includes a plurality of elements, is displayed such that an element represents a medical examination. A position of an element on the timeline indicates an acquisition time for a medical examination relative to other medical examinations on the timeline. In general, an element displays information about a corresponding medical examination.

In one embodiment, the timeline comprises a patient history timeline. The elements of a patient history timeline collectively represent a history of medical examinations for a patient. In another embodiment, the timeline comprises a relevant examination timeline. The elements of a relevant exam timeline represent medical examinations relevant to current exams displayed on the user interface.

In one embodiment, the medical information displayed in an element comprises: a date, to indicate acquisition of the medical examination; information to indicate whether images are available for the corresponding medical examination; and information to indicate whether a report is available for the corresponding medical examination. In addition, a user may extract information about an exam through use of a cursor control device, including: information to indicate a location of images for a medical examination; general information about the medical examination; and a plurality of menu items to permit a user to select functions for the medical examination.

In another embodiment, a computer readable medium comprising a plurality of instructions, which when executed by a computer, causes the computer to perform the steps of: displaying, on an output display, medical information for a medical informatics system, said medical information including information regarding medical examinations available within said medical informatics system; displaying a timeline comprising a plurality of elements, such that an element represents a medical examination, a position of an element on said timeline indicating an acquisition time for a medical examination relative to other medical examinations on said timeline; displaying, within an element on said timeline, information about a corresponding medical examination; and displaying images associated with at least two selected medical examinations.

BRIEF DESCRIPTION OF THE DRAWINGS

FIG. 2 illustrates examination timelines for some examinations that do not have corresponding images.

FIG. 3 illustrates background information for a medical exam to indicate whether a report is associated with the exam.

FIG. 4 illustrates one embodiment for displaying a location of images for a corresponding medical exam.

DETAILED DESCRIPTION

Overview of A Medical Informatics User Interface

An examination timeline is displayed in connection with a user interface. In one embodiment, the user interface for a medical informatics system permits a physician to work with digitized medical images in a manner that the physician is accustomed to working with traditional analog film. The user interface provides the user to ability to select exams, which consist of medical images and series, for patients. In one embodiment, the user selects exams on the user interface through a patient browser view.

Figure 1:
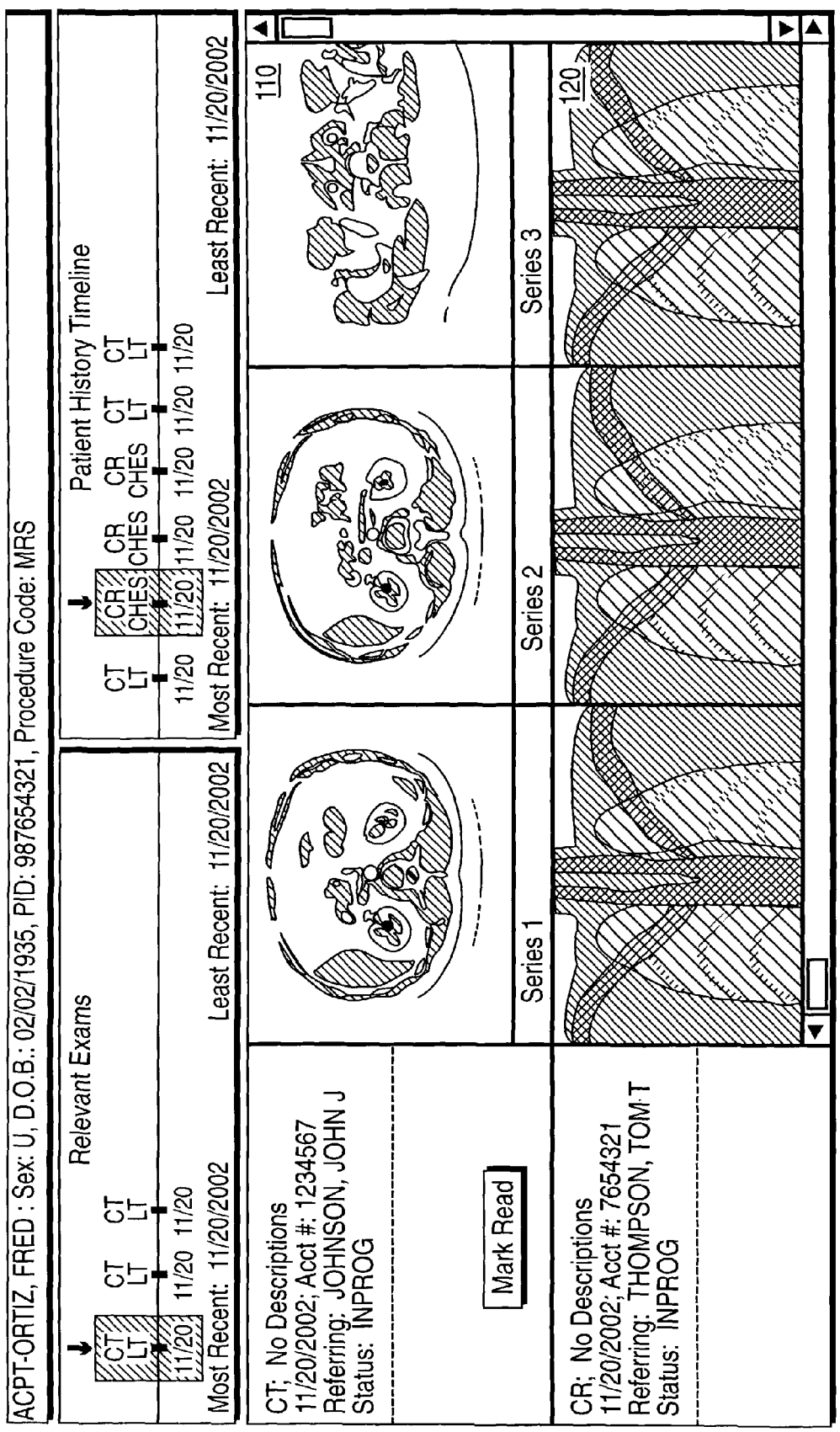
FIG. 1 illustrates one embodiment for displaying examination timelines within a medical informatics user interface.

The medical informatics user interface permits a user to organize and navigate images/series for selected exams. FIG. 1 illustrates an example medical informatics user interface in accordance with one embodiment of the present invention. The user interface includes a plurality of exams for the selected patient. For the example of FIG. 1, two exams, arranged vertically on the screen, are shown. In one embodiment, exams (110 and 120) are automatically laid out chronologically from top to bottom on the medical informatics user interface (i.e., the exams are laid out from the newest at the top to the oldest at the bottom). In another embodiment, the exams are laid out from left to right.

Each exam is broken out left to right into one or more series for CT/MR and one or more images for CR/DR. In the example of FIG. 1, the first or top exam 110 includes the series of images labeled Series 1, Series 2, and Series 3. The second exam 120, displayed on the second rack of the medical informatics user interface, currently displays three (3) images.

In one embodiment, the medical informatics user interface is displayed in a standard orientation such that each horizontal scroll bar contains an exam. The user, using the horizontal scroll bar, is permitted to scroll left and right to prompt the system to display the series/images contained within the exam. Also, a single vertical scroll bar (e.g., on the right of the display) is provided to permit the user to scroll, in a vertical direction (i.e., from top to bottom), to display multiple exams.

The user may also use the features of the medical informatics user interface to organize images, within an exam, by re-arranging the relative horizontal positions among the images/series within an exam. In one embodiment, these organization operations are executed via a drag and drop operation. In a drag and drop operation, the user "selects" a series/image or exam with the cursor control device, and drags the series/image or exam to the destination location. When the image is located at the destination location, the user releases the series/image or exam to complete the drag and drop operation. When a user drags an image to a new location and drops the image over a second image, the system swaps the two images on the display. For example, if the system horizontally displays images 1, 2, 3, 4, 5 for an exam, and the user drops image #5 onto image #3, the system displays the images in the new order of 1, 2, 5, 4, 3.

In one embodiment, a control monitor and user input device(s) are provided for use with the computer workstation to select medical images or series of medical images for viewing on one or more monitors. The control monitor may be used in a diagnostic system. In general, the control monitor displays a plurality of images/series to allow the user of the computer workstation to select specific images for display on the monitors. In one embodiment, the control monitor displays a user interface, such as the user interface shown in FIG. 1.

Medical Examination Timelines:

FIG. 1 illustrates one embodiment for displaying examination timelines within a medical informatics user interface. For this embodiment, the examination timeline includes "Relevant Exams" and "Patient History Timeline." In general, the "Relevant Exams" timeline identifies to the user of the medical informatics system prior relevant examinations for a selected patient. The Patient History Timeline provides a history of examinations for the current patient.

The examination timeline includes a plurality of elements, arranged on a horizontal timeline, that correspond to medical examinations (or exams). For purposes of nomenclature, an element refers to information displayed on a timeline for a particular medical examination. For example, the element for the second medical exam displayed on the patient history timeline of FIG. 1 includes the information CR (modality), CHES (body area), and date (11/20).

For this embodiment of the user interface, the examination timeline is displayed on a medical informatics user interface. For the embodiment of FIG. 1, the examination timelines are displayed near the top of the user interface display, with the Relevant Exams and Patient History Timelines arranged horizontally (e.g., the Patient History Timeline is situated to the right of the Relevant Exams timeline). The general purpose of the examination timelines is to present a list of patient exams to the user of the medical informatics system. Examinations are sorted based on the examination date. Examinations are displayed from left to right with the most recent examinations displayed on the left side of the timeline.

An examination has a blue/gray colored background if that exam has been loaded into an image display rack. The blue/gray color is illustrated in FIG. 1 with a background pattern. For the example Patient History Timeline of FIG. 1, the "CR CHES" exam from 11/20 is loaded into rack 120 of the user interface display, and the "CT LT" exam from 11/20 is loaded into rack 110 of the user interface display.

Figures 2, 3, 4:
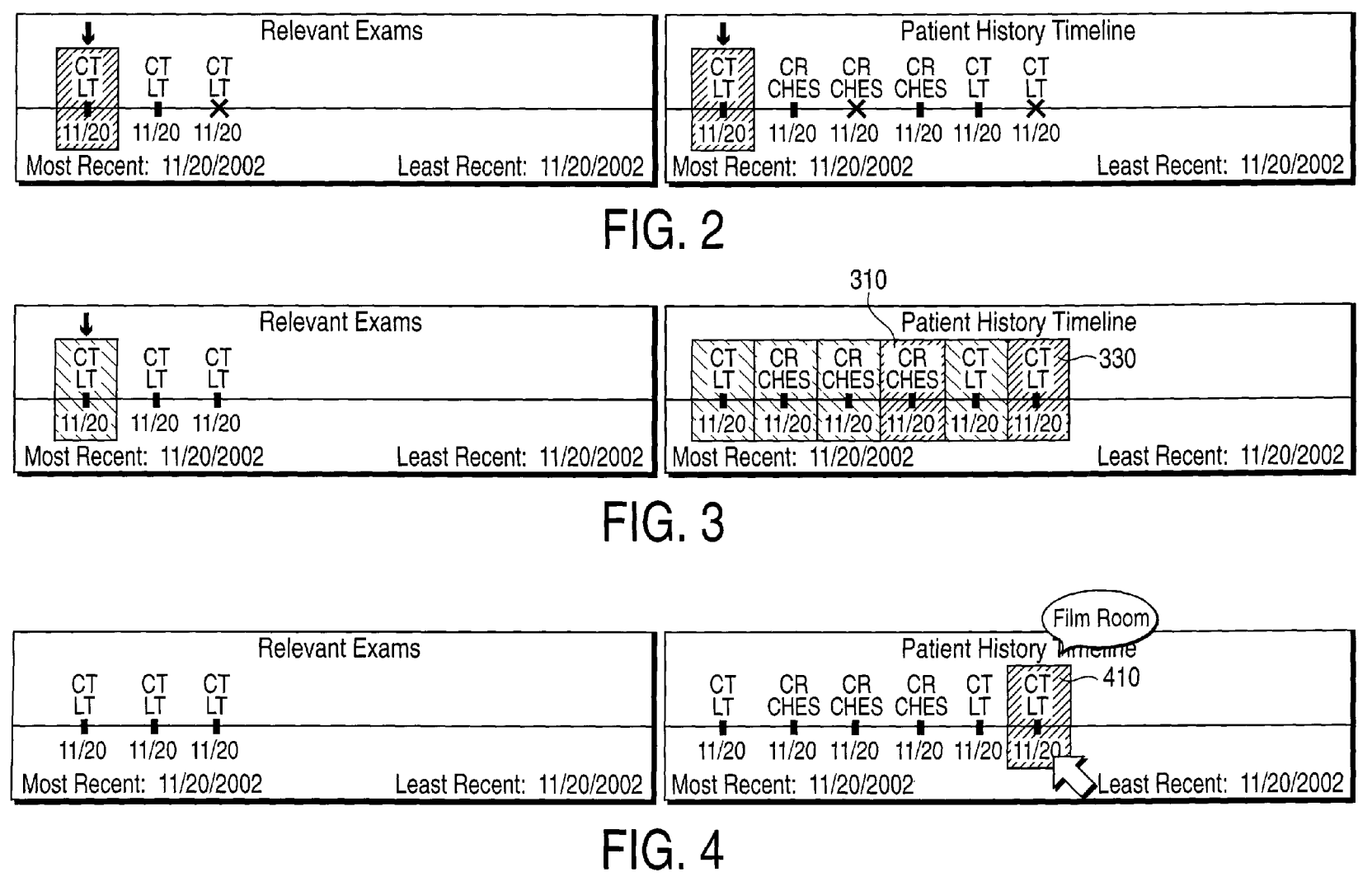

In one embodiment, each examination in the timeline displays the following items in this order from top to bottom. First, if images are present for the identified examination, a straight line is displayed over the horizontal timeline. If no images are present for the identified examination, an X is displayed over the horizontal timeline. FIG. 2 illustrates examination timelines for some examinations that do not have corresponding images. As shown in FIG. 2, the element for the third exam (i.e., left to right) on the Relevant Exams timeline does not have images immediately accessible to the medical informatics system (i.e., the images may be stored on an archive coupled to the medical informatics system). Also, the third and sixth elements (i.e., left to right) on the Patient History Timeline do not have images associated with the medical exams.

Second, the month and date of exam is displayed beneath the horizontal timeline (e.g., 11/20 for November 20). If an examination does not have a report, the examination text is displayed in blue. If an examination has a report, then the examination text is displayed in black. FIG. 3 illustrates background information for a medical exam that indicates whether a report is associated with the exam. For the example embodiment of FIG. 3, elements 310 and 330 are shaded to indicate that the corresponding medical examinations do not include reports. All other exam elements displayed on the timelines are shaded to indicate that the associated medical exams have reports.

If an examination has a report but no images, the call-out box that appears when placing the mouse over the pictogram indicates the location of the images (e.g., film room). FIG. 4 illustrates one embodiment for displaying a location of images for a corresponding medical exam. The element 410 indicates that the corresponding exam does not include images. For the embodiment of FIG. 4, a user places a cursor, using a cursor control device, over the element (410), and a call-out box indicates that the images are located in a film room (e.g., a film room for a hospital).

If the user depresses a button on a cursor control device (e.g., a left mouse click) while placing the cursor over an exam that has analog images (i.e., the images are not digital and available on the medical informatics system), an option is presented to the user to send an e-mail to the film room or print a film-request on a printer located in the film-room. If a study is not on-line (i.e., the study is not immediately accessible to the medical informatics system), but has digital images on a customer's traditional PACS system, the medical informatics system automatically spawns a DICOM Query to the archive and displays a dialog-box to the user stating "The study that you have selected is stored on another system, the retrieval of this study may take up to several minutes, would you like to proceed." The user then has the option to continue or cancel.

In one embodiment, if the user moves the cursor over an examination element on the timeline, a tool tip containing the following data is displayed.

| | |
|---|---|
| Acc #: | (Accession Number) |
| Date/Time: | MM/DD/YYYY |
| | HH:MM:SS of exam |
| Ref. Physician | (referring physician) |
| Procedure Description: | Procedure Description |
| Status: | Exam Status |

Figure 5:
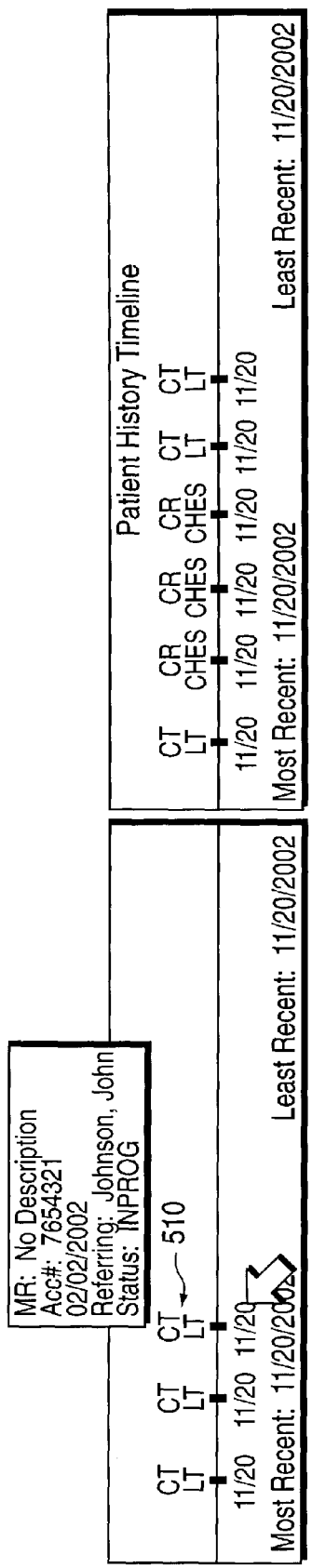
FIG. 5 illustrates displaying information for an exam selected with a cursor control device.

FIG. 5 illustrates displaying information for an exam selected with a cursor control device. For the example of FIG. 5, the user places the cursor over element 510 on the Relevant Exams timeline, and in response, the system displays general information for the exam corresponding to element 510

If the user selects a predetermined button (e.g., right clicks) while placing the cursor over an examination in the timeline using a cursor control device, the following menu items are displayed.

"Unload Exam"—Disabled if exam has not been loaded into the rack. If selected, removes the exam from the rack.

"Show Report"—Disabled if exam has no report. If selected, displays the clinical exam notes for this report.

"Order Film"—Disabled if exam has images. If selected, allows user to order film.

"Query"—Enabled if exam has no images and exam has report. If selected, opens iQuery dialog and queries for that exam.

"Send via DICOM"—Enabled if exam has images. If selected spawns the DICOM Send dialog.

Figure 6:
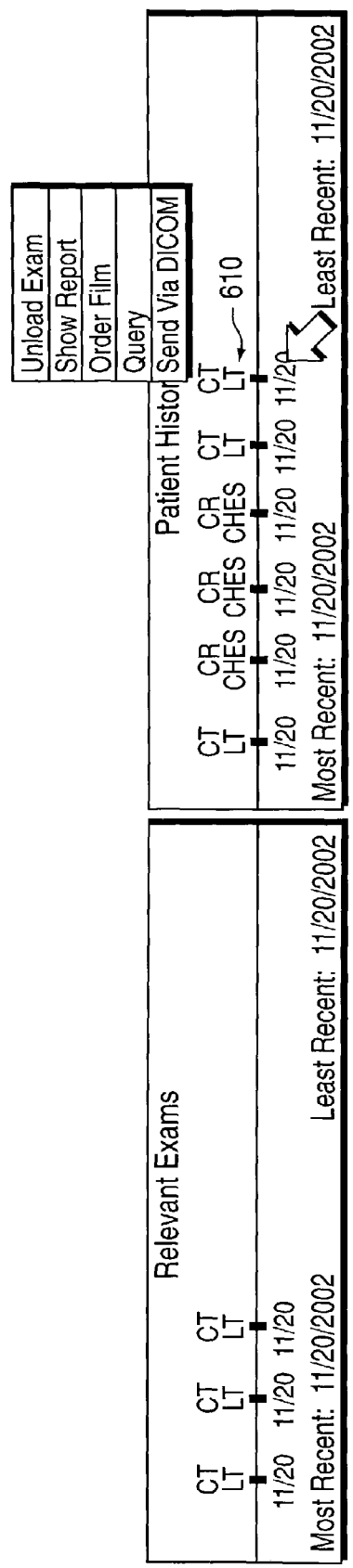
FIG. 6 illustrates one embodiment for presenting menu items to a user for a selected exam.

FIG. 6 illustrates one embodiment for presenting menu items to a user for a selected exam. For this embodiment, the user places a cursor over element 610, and right clicks a button on the cursor control device. In response, the system displays a menu of items as shown in FIG. 6.

In one embodiment, if the user of the medical informatics system presses a button on a cursor control device (e.g., left clicks) with the cursor placed over an exam element, the system executes the following. If the exam is scheduled, a dialog containing the protocol worklist is presented. If the exam has images, those images are loaded into the user interface rack and made visible on the user interface. If the exam has no images, but has a report, the iQuery dialog is presented allowing the user to fetch that exam. Also, dragging the middle mouse button allows the user to scroll the timeline to view exams.

Within the representative highlighted relevant timeline, an algorithm determines the logical priors, loaded on the diagnostic monitors, and represents these exams on the examination timeline by coloring the study date and modality in a red color. In one embodiment, the system selects exams for placement of the Relevant Exams timeline based on the body part of exams currently loaded on the user interface. For example, if the user interface currently displays MR exams of the brain, the exam elements displayed on the Relevant Exams timeline include examination of the brain. In addition, in one embodiment, the system uses a body part dictionary to include other body parts closely related to the current exams. For example, if the current exams cover the brain, the body part dictionary expands the body parts to include all exams that cover the scull area for inclusion on the Relevant Exams timeline.

Exams created in different years are separated by a vertical dashed line with the last two digits of the exam date year on either side of the line. This is displayed in the same area as the exam date (e.g., 99|00).

The scale of timelines, prior to scrolling by the user, consists of 50% max relevant and 50% max prior.

When the user moves the cursor over an exam in the timeline that has been loaded into the rack, the rack shelf is highlighted. In one embodiment, the rack shelf is highlighted through display of a white rectangle around the shelf. When a user moves the cursor over a shelf in the rack, an arrow will be draw above the entry in the timeline.

Although the present invention has been described in terms of specific exemplary embodiments, it will be appreciated that various modifications and alterations might be made by those skilled in the art without departing from the spirit and scope of the invention.

What is claimed is:

1. A method for displaying medical information, said method comprising:

displaying, on an output display, medical information for a medical informatics system, said displayed medical information including one or more images of anatomical structure of a patient available within said medical informatics system;

displaying, concurrently with displaying the medical information, a timeline comprising a plurality of elements, wherein an element represents a medical examination of the patient, and a position of the element on said timeline indicates an acquisition time of the medical examination corresponding to the element relative to a second medical examination of the patient represented by a second element on said timeline; and displaying, inside a perimeter of the element displayed on said timeline, information about the medical examination, including imaging information about at least one of the displayed images of the anatomical structure of the patient.

2. The method as set forth in claim 1, wherein displaying the timeline comprises displaying a first timeline comprising a plurality of elements representing a history of medical examinations for the patient.

3. The method as set forth in claim 2, wherein displaying the timeline comprises concurrently displaying a second timeline comprising a plurality of elements representing medical examinations relevant to an anatomical structure in an image displayed on said output display, wherein the plurality of elements of the second timeline are a subset of the plurality of elements of the first timeline.

4. The method as set forth in claim 1, wherein displaying the information about the medical examination comprises displaying an acquisition date of the image of the medical examination.

5. The method as set forth in claim 1, wherein displaying the information about the medical examination comprises displaying information indicative of whether the image of the medical examination is available for display on the output display.

6. The method as set forth in claim 1, wherein displaying the information about the medical examination comprises displaying information that indicates a report is available for the corresponding medical examination.

7. The method as set forth in claim 1, wherein displaying the information about the medical examination comprises displaying information that indicates a physical location of images for a medical examination which are not available for display.

8. The method of claim 7, further comprising sending a notification to request the images located at the physical location.

9. The method of claim 8, further comprising providing a user with a message indicating that requested images are stored in another system.

10. The method of claim 9, wherein the message further indicates that retrieval of the requested images may take additional time.

11. The method of claim 10, wherein the message further includes a query whether to proceed with the retrieval of the requested images.

12. The method as set forth in claim 1, wherein displaying the information about the medical examination comprises:
receiving cursor position information that indicates a cursor is located over an element displayed for a medical examination; and
displaying, in response to said cursor position information, additional information about said medical examination.

13. The method as set forth in claim 1, wherein displaying the information about the medical examination comprises:
receiving cursor position information that indicates a cursor is located over an element displayed for a medical examination;
receiving input control information that indicates a button has been selected on a user input device; and
displaying around said element for said medical examination, in response to said cursor position information and said input control information, additional information about said medical examination.

14. The method as set forth in claim 1 wherein displaying the information about the medical examination comprises:
receiving cursor position information that indicates a cursor is located over an element displayed for a medical examination;
receiving input control information that indicates a button has been selected on a user input device; and
displaying, around said element for said medical examination, in response to said cursor position information and said input control information, a plurality of menu items to permit a user to select functions for said medical examination.

15. The method of claim 1, further comprising concurrently displaying a subset of the plurality of elements on the timeline on a second timeline and the plurality of elements on the timeline.

16. The method of claim 15, wherein the subset includes elements corresponding to medical examinations of a same first body part.

17. The method of claim 16, wherein the subset further includes elements corresponding to medical examinations of a second body part that provides further information about the first body part.

18. The method of claim 17, further comprising determining the second body part using a dictionary that inter-relates body parts.

19. The method of claim 1, wherein at least two of the plurality of elements are displayed differently on said timeline.

20. The method of claim 1, wherein the element is a graphical icon and the information displayed inside the perimeter of the element is part of the element.

21. A computer readable storage medium comprising a plurality of instructions, which when executed by a computer, causes the computer to perform the steps of:
displaying, on an output display, medical information for a medical informatics system, said displayed medical information including one or more images of a patient available within said medical informatics system;
displaying, concurrently with displaying the medical information, a timeline comprising a plurality of elements, wherein an element represents a medical examination of the patient, and a position of an element on said timeline indicates an acquisition time for the medical examination corresponding to the element relative to a second medical examination of the patient represented by a second element on said timeline; and
displaying, inside a perimeter of the element displayed on said timeline, information about the medical examination, including information about at least one of the displayed images of the patient.

22. The computer readable medium as set forth in claim 21, wherein the step of displaying the timeline comprises concurrently displaying a patient history timeline comprising a plurality of elements representing a history of medical examinations for the patient and a relevant examination timeline comprising a plurality of elements representing medical examinations relevant to medical examinations displayed on said output display.

23. The computer readable medium as set forth in claim 21, wherein the one or more images of the patient includes one or more diagnostic images of anatomical structure of the patient.

24. The computer readable medium as set forth in claim 21, wherein the step of displaying information about the corresponding medical examination comprises at least one of displaying a date to indicate acquisition of said medical examination or displaying information to indicate whether images are available for the corresponding medical examination.

25. The computer readable medium as set forth in claim 21, wherein the one or more images of the patient includes at least two images of the patient respectively generated from data from two different imaging examinations.

26. The computer readable medium as set forth in claim 21, wherein the step of displaying information about the corresponding medical examination comprises displaying indicia indicative of a type of imaging modality of the medical imaging examination.

27. The computer readable medium as set forth in claim 21, wherein the step of displaying information about the corresponding medical examination comprises at least one of displaying information to indicate a location of images for a medical examination or displaying information to indicate whether a report is available for the corresponding medical examination.

28. The computer readable medium as set forth in claim 21, wherein the step of displaying information about the corresponding medical examination comprises the steps of:
receiving cursor position information that indicates a cursor is located over an element displayed for the medical examination; and
displaying, in response to said cursor position information, additional information about said medical examination.

29. The computer readable medium as set forth in claim 21, wherein the step of displaying information about the corresponding medical examination comprises the steps of:
receiving cursor position information that indicates a cursor is located over an element displayed for the medical examination;
receiving input control information that indicates a button has been selected on a user input device; and
displaying around said element for said medical examination, in response to said cursor position information and said input control information, additional information about said medical examination.

30. The computer readable medium as set forth in claim 21, wherein the step of displaying information about the corresponding medical examination comprises the steps of:
  receiving cursor position information that indicates a cursor is located over an element displayed for the medical examination;
  receiving input control information that indicates a button has been selected on a user input device; and
  displaying, around said element for said medical examination, in response to said cursor position information and said input control information, a plurality of menu items to permit a user to select functions for said medical examination.

31. A computer system comprising:
  an output display for displaying medical information for a medical informatics system; and
  a processor, coupled to said output display, for displaying, on said output display, information regarding medical examinations available within said medical informatics system, for displaying a timeline comprising a plurality of elements, wherein an element represents a medical examination and presents information about at least one concurrently displayed image of anatomy of a patient of the medical examination, and a position of an element on said timeline indicating an acquisition time for a medical examination relative to other medical examinations on said timeline, and for displaying images of anatomy of the patient, including the at least concurrently displayed image of anatomy of the patient, corresponding to at least two of the medical examinations.

32. The computer system of claim 31, wherein the processor is configured to display portions of the plurality of elements on the timeline including related medical examinations on a relevant examination timeline.

33. The computer system of claim 32, wherein the portions are related based on a body part of one of the at least two selected medical examinations.

34. The computer system of claim 31, wherein the processor is configured to display a selected medical examination differently from the other medical examinations on said timeline.

35. A method for displaying medical information comprising:
  concurrently displaying a first timeline and a second different timeline, the first timeline displaying a history of medical examinations of a patient, including information about a concurrently displayed image of a region of anatomy of the patient, wherein the image has diagnostic value; and the second timeline displaying a subset of the first timeline.

36. The method of claim 35, wherein the subset includes medical examinations of the history of medical examination that correspond to a selected region of interest of the patient.

37. The method of claim 35, wherein the subset of medical examinations are related based on a body part of a selected medical examination and other body parts related to the body part.

38. The method of claim 37, further comprising the act of determining the other body parts using a dictionary that includes body parts.

39. The method of claim 35, further comprising the act of displaying a selected medical examination differently from other medical examinations on the history timeline.

40. The method of claim 39, further comprising the act of displaying images associated with the selected medical examination.

41. The method of claim 35, further comprising the acts of:
  selecting a medical examination from one of the history timeline and the relevant timeline;
  displaying in a rack images associated with the selected medical examination; and
  highlighting the rack when a cursor is positioned over the selected medical examination.

42. The method of claim 35, further comprising the acts of:
  selecting a medical examination from one of the history timeline and the relevant timeline; and
  displaying the selected medical examination differently from other medical examinations on the history timeline and the relevant timeline.

43. The method of claim 35, further comprising the act of displaying information about a selected medical examination to indicate a physical location of images for the selected medical examination which are not available for display.

44. The method of claim 43, further comprising the act of sending a notification to request the images located at the physical location.

45. The method of claim 44, further comprising the act of providing a message indicating that requested information are stored in a system different from a current system.

46. The method of claim 45, wherein the message further indicates that retrieval of the requested information may take additional time.

47. The method of claim 46, wherein the message further includes a query whether to proceed with the retrieval of the requested information.

48. The method of claim 35, further comprising the acts of:
  displaying images associated with the selected medical examination including a first image located at a first position and a second image located at a second position; and
  dragging and dropping the first image over the second image so that the first image moves to the second position and the second image moves to the first position.

* * * * *